United States Patent
Medes et al.

(10) Patent No.: US 7,253,824 B2
(45) Date of Patent: Aug. 7, 2007

(54) METHOD AND APPARATUS OF PROVIDING WAVEFRONT COLOR THERAPY

(76) Inventors: Dara C. Medes, 15 N. Pease Rd., Woodbridge, CT (US) 06525; Heather Lyn Medes, 15 N. Pease Rd., Woodbridge, CT (US) 06525; William V. Padula, 37 Soundview Rd., Guilford, CT (US) 06437

( * ) Notice: Subject to any disclaimer, the term of this patent is extended or adjusted under 35 U.S.C. 154(b) by 700 days.

(21) Appl. No.: 10/713,912

(22) Filed: May 2, 2003

(65) Prior Publication Data
US 2006/0106436 A1    May 18, 2006

(51) Int. Cl.
G09G 5/10    (2006.01)

(52) U.S. Cl. .................. 345/690; 607/88; 128/898

(58) Field of Classification Search ................ 345/204, 345/690; 362/230, 231; 607/88, 89–94; 128/898
See application file for complete search history.

(56) References Cited

U.S. PATENT DOCUMENTS

| | | | |
|---|---|---|---|
| 6,007,569 A * | 12/1999 | Frenkel et al. ................ 607/88 |
| 6,357,889 B1 * | 3/2002 | Duggal et al. ................ 362/84 |
| 6,676,284 B1 * | 1/2004 | Wynne Willson ........... 362/555 |
| 7,014,336 B1 * | 3/2006 | Ducharme et al. ........... 362/231 |
| 2005/0195598 A1 * | 9/2005 | Dancs et al. ................ 362/231 |

* cited by examiner

*Primary Examiner*—Amr A. Awad
*Assistant Examiner*—Tom V. Sheng
(74) *Attorney, Agent, or Firm*—Koda & Androlia

(57) ABSTRACT

A method and apparatus of providing wave-front color therapy using a computer or portable handheld devices such as PDA's and other portable telecommunication devices to deliver a specific different nanometer wavelength of light to affect a wide variety of visual, binocular, function, perceptual, and cognitive-related vision imbalances that interfere with function and performance. The current proposed device would provide specific treatment for these difficulties by delivering different wavelengths of light through a computer monitor. The exact therapeutic prescription including nanometer specifications and hue-saturation will be prescribed for individuals with a wide range of visual problems caused by a traumatic brain injury, cerebrovascular accident, and Multiple Sclerosis, and the like, to name a few examples. This disclosure claims analog and digital relations of light as it relates to both the spatial and temporal relationship of light.

15 Claims, 4 Drawing Sheets

Full Spectrum of Visible Light

Combinations include the entire circuit of the visible color spectrum in any direction, as well as going from one color's range to a second color or through the range of a third color or fourth color. Some basic examples include:

| | | | |
|---|---|---|---|
| Violet to Indigo | Blue to Indigo | Yellow to Blue | Red to Green |
| Violet to Blue | Blue to Green | Yellow to Green | Red to Yellow |
| Violet to Green | Blue to Yellow | Yellow to Orange | Red to Orange |
| Violet to Yellow | Blue to Orange | Yellow to Red | Red to White |
| Violet to Orange | Blue to Red | Yellow to White | Red to Black |
| Violet to Red | Blue to White | Yellow to Black | White to Black |
| Violet to White | Blue to Black | Orange to Violet | White to Red |
| Violet to Black | Green to Violet | Orange to Indigo | White to Orange |
| Indigo to Violet | Green to Indigo | Orange to Blue | White to Yellow |
| Indigo to Blue | Green to Blue | Orange to Green | White to Green |
| Indigo to Green | Green to Yellow | Orange to Yellow | White to Blue |
| Indigo to Yellow | Green to Orange | Orange to Red | White to Indigo |
| Indigo to Orange | Green to Red | Orange to White | White to Violet |
| Indigo to Red | Green to White | Orange to Black | Black to White |
| Indigo to White | Green to Black | Red to Violet | |
| Indigo to Black | Yellow to Violet | Red to Indigo | |
| Blue to Violet | Yellow to Indigo | Red to Blue | |

Figure 1 – Full Spectrum of Visible Light

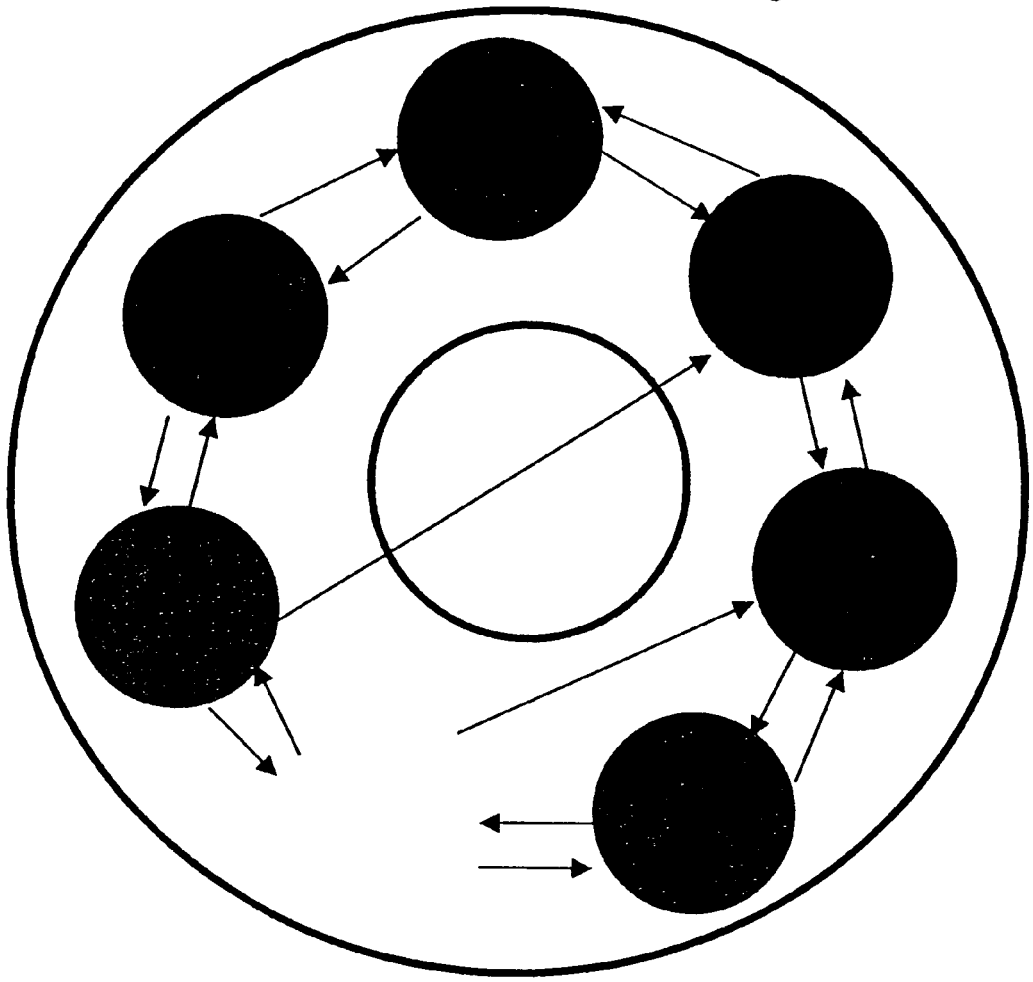

Combinations include the entire circuit of the visible color spectrum in any direction, as well as going from one color's range to a second color or through the range of a third color or fourth color. Some basic examples include:

| | | | |
|---|---|---|---|
| Violet to Indigo | Blue to Indigo | Yellow to Blue | Red to Green |
| Violet to Blue | Blue to Green | Yellow to Green | Red to Yellow |
| Violet to Green | Blue to Yellow | Yellow to Orange | Red to Orange |
| Violet to Yellow | Blue to Orange | Yellow to Red | Red to White |
| Violet to Orange | Blue to Red | Yellow to White | Red to Black |
| Violet to Red | Blue to White | Yellow to Black | White to Black |
| Violet to White | Blue to Black | Orange to Violet | White to Red |
| Violet to Black | Green to Violet | Orange to Indigo | White to Orange |
| Indigo to Violet | Green to Indigo | Orange to Blue | White to Yellow |
| Indigo to Blue | Green to Blue | Orange to Green | White to Green |
| Indigo to Green | Green to Yellow | Orange to Yellow | White to Blue |
| Indigo to Yellow | Green to Orange | Orange to Red | White to Indigo |
| Indigo to Orange | Green to Red | Orange to White | White to Violet |
| Indigo to Red | Green to White | Orange to Black | Black to White |
| Indigo to White | Green to Black | Red to Violet | |
| Indigo to Black | Yellow to Violet | Red to Indigo | |
| Blue to Violet | Yellow to Indigo | Red to Blue | |

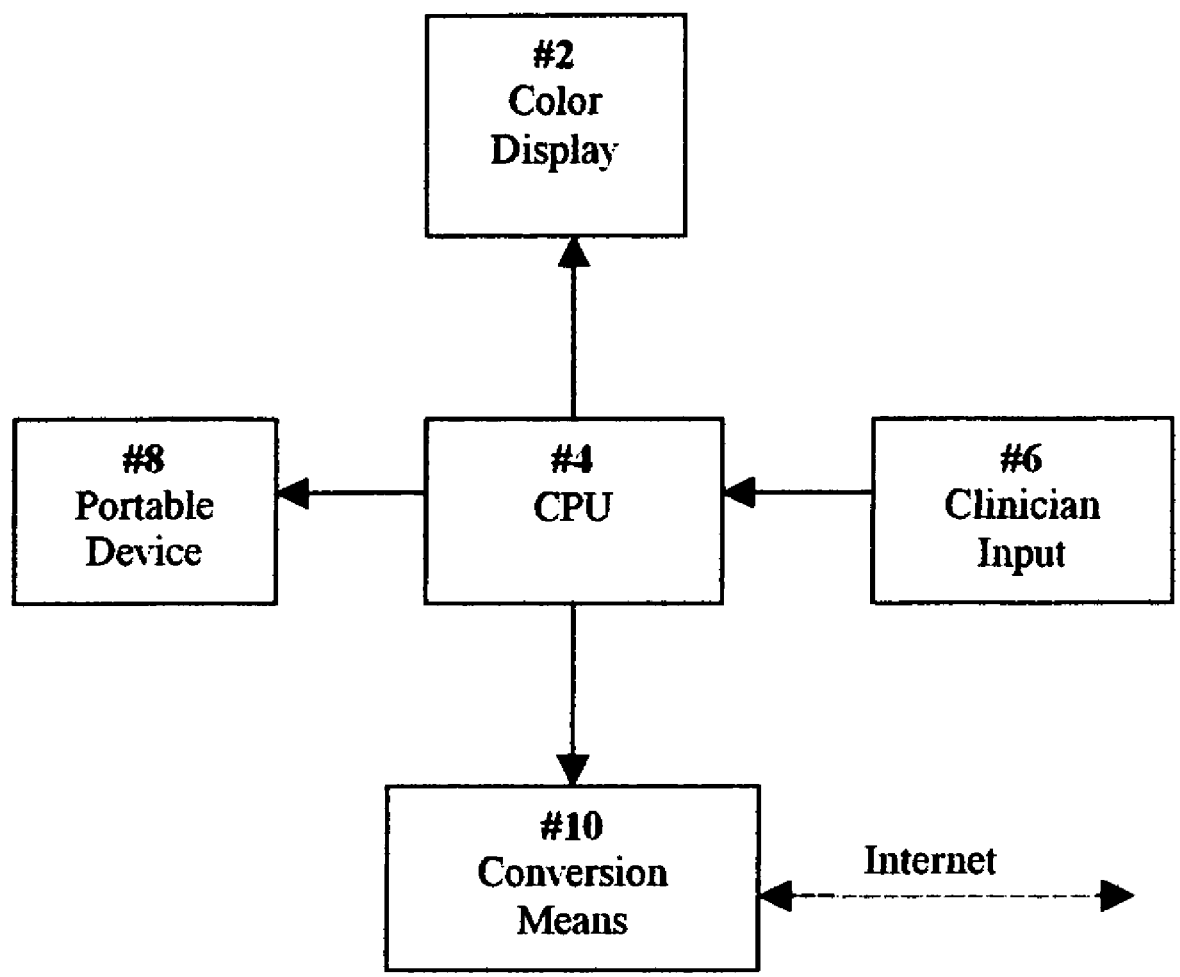

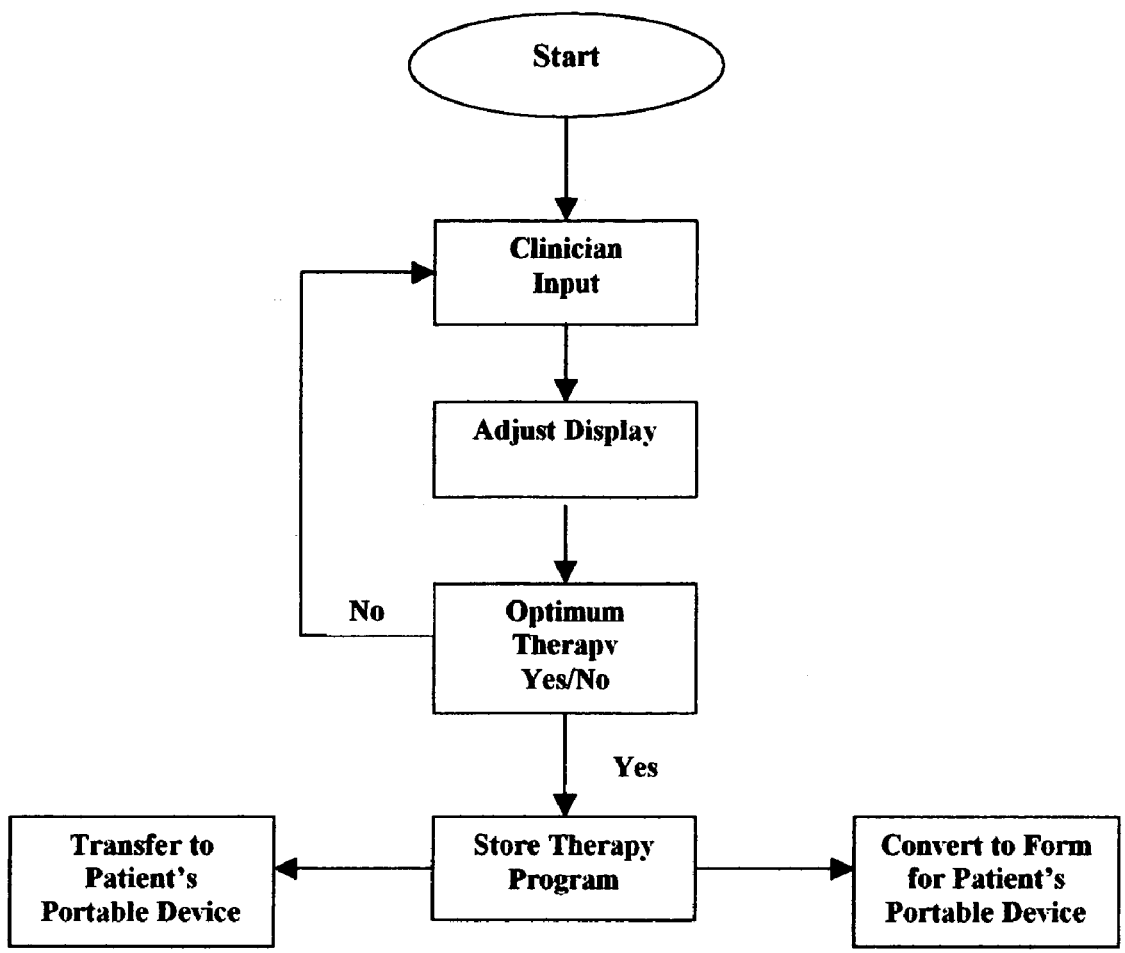

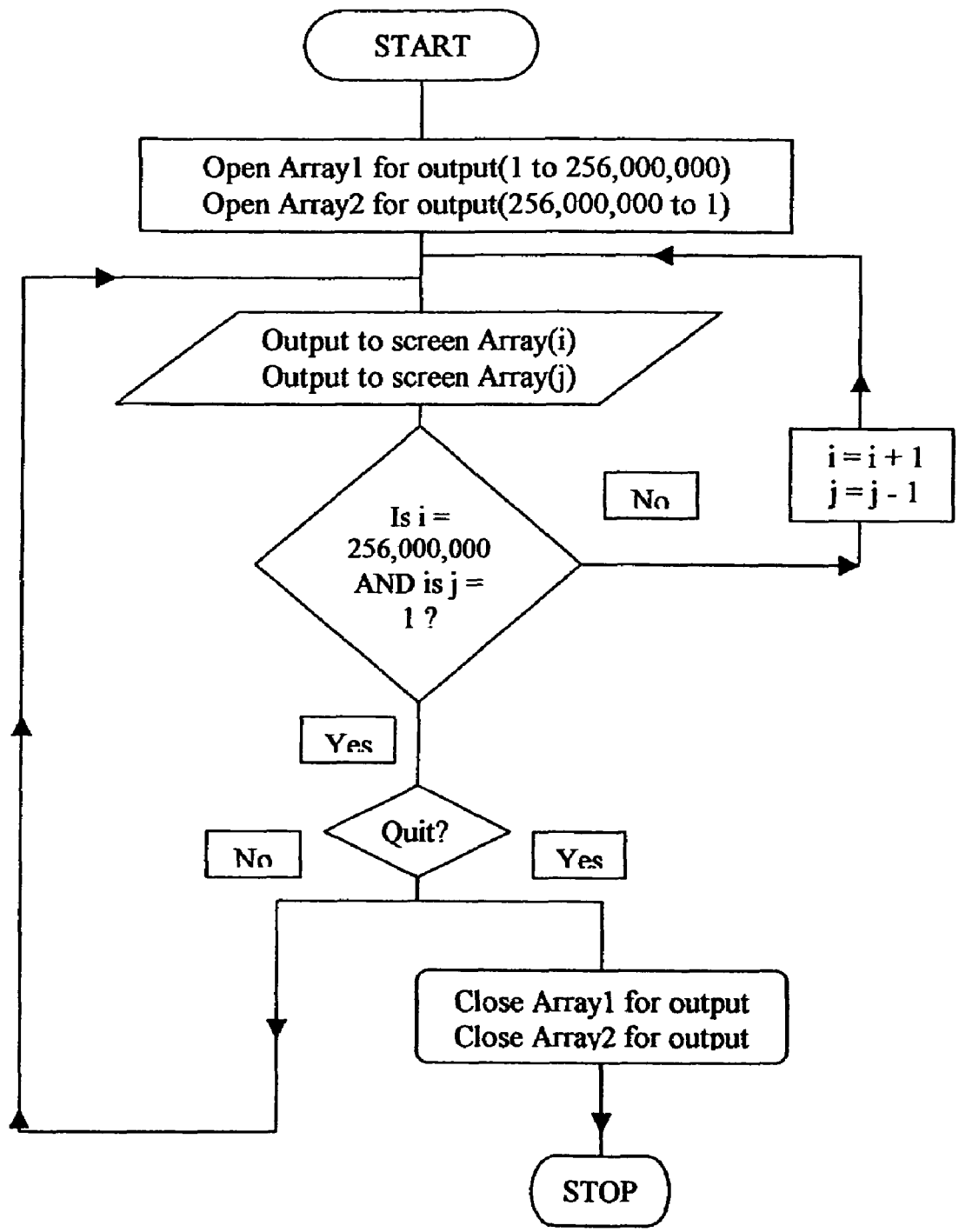

METHOD AND APPARATUS OF PROVIDING WAVEFRONT COLOR THERAPY

BACKGROUND OF THE INVENTION

1. Field of Invention

The invention relates to human/computer interfaces on portable devices such as PDA's and other similar telecommunication systems, to provide portable software systems intended for rehabilitation by means of color therapy.

2. Prior Art

Prior art is divided into three primary categories, diagnostic tools, rehabilitation treatment methods, and previously designed light therapy treatment methods.

The first area of prior art is the manner of diagnostic tools used in the development of wave-front color therapy in conjunction with therapeutic prescriptions. To date, color therapy in conjunction with therapeutic prescription use has been a manual, often tedious process not capable of pinpointing the precise nanometer of a color's wavelength best suited for the patient's use.

The second area of prior art is the manner of rehabilitation treatment methods for neurological impairments such as stroke, brain injury, CVA, and MS to name several, and learning disabilities such as Attention Deficit Disorder, and ADHD.

There is a host of computer based, non-portable, dumb-terminal rehabilitation systems used within the structure of cognitive, vision and learning disability rehabilitations. They are geared at re-training the impaired or injured neurological processes.

Unfortunately, there are two basic shortcomings to the conventional approach of neurological rehabilitations. These machines are only available to the rehabilitation facility due to cost and size and are therefore not available for private patient consumer use. This limits the amount of time a patient can spend using these rehabilitation tools due to a number of factors, as set forth below.

First, a patient who is a candidate for neurological rehabilitation is often also attending physical and occupational therapies, recovering from surgeries or other treatments and procedures associated with their neurological assault. During the time crucial window of cognitive and visual rehabilitation, a patient's day is consumed with therapies and doctors visits, often leaving the time that can be spent on cognitive rehabilitation shortchanged or even completely neglected.

Second, the neurologically impaired patient's rehabilitation is also subject to the schedules of their caretakers as they are often unable to transport themselves, inclement weather, flare-up of injuries, or office scheduling conflicts.

Despite the enormous amount of time devoted to the rehabilitation process involving doctors and rehabilitation specialists, a patient spends a great deal of time waiting in medical waiting rooms, waiting for transportation between appointments, and at the end of the day, is often too exhausted to attend to cognitive rehabilitation and the associated exercises. This time can be recaptured with a portable rehabilitation device to make best use of spare time to become rehabilitation time.

A patient who does not face the aforementioned problems can also use this device to maximize their rehabilitation, reducing rehabilitation expense while making best use of the window of maximum rehabilitative progress.

Third, a fundamental problem in the conventional approach is that is does not fully take into account the need of the learning impaired student.

A learning impaired student is paired with a learning specialist during school hours, which either robs time from their education or uses their break periods, leaving an already overworked student without a break during the day. The second approach is to team a student with a learning specialist after school, taking time away from homework and putting a student further behind in their work.

Any adaptive technology devices that a mainstreamed student may be offered might not be available in all schools, and a student may often be embarrassed to use them in front of others students who may perceive a learning disability as a lack of intelligence on the part of the disabled student. Fear of such a perception may render a student reluctant or too embarrassed to use the adaptive tech tools designed to help them.

Color Therapy has long been used medically. Color, or Light Therapy is used for a number of purposes, including, Seasonal Affected Disorder (SAD), dermatological purposes, cosmetic enhancement, as well as for Syntonic Optometry. The latter has been used for the past 70 years for treatment of several optometric disorders. Recently, it has been shown to be helpful in the diagnosis and treatment of brain injuries, Cerebro-vascular accidents (CVA), and other neurological disorders.

There are, however, several failings of the treatments and therapies developed to date:

1) White light machines.

Many light machines emit full spectrum white light, not specific and finite wavelengths.

There are multiple benefits to being able to isolate a finite wavelength, as in the case of this claimed computer program:

a. The white light machines available today, by their very nature, emit all wavelengths in the visible spectrum. For as therapeutic as certain wavelengths of color can be to a patient, another wavelength could be harmful or uncomfortable, and there is no way to omit the uncomfortable or harmful wavelengths from a white-light machine and only use the helpful ones for therapy.

b. Many patients who suffer neurological problems suffer from photophobia, or sensitivity to light and glare. While some white light machines have a dimmer, this may not reduce brightness and glare enough for the patient and cause discomfort, and would not be therapeutic.

c. Since all colors are emitted from a white light machine, it is impossible to determine what wavelengths could be most helpful to the patient. In contrast, this computer program can isolate the exact wavelength of color that is beneficial to the patient.

d. White light machines often require extended periods of time per day to receive therapeutic benefit. By this program isolating to the most therapeutic range of wavelengths, the patient will receive the most precise diagnosis and the best therapy for their specific disorder in the shortest amount of time. This is essential as there is a limited window of time after neurological injury or onset of a neurological illness that a patient has to capture the majority of recovery they will make—thus, time is of the essence.

2) Methods of color therapy developed to date that isolate certain color spectrums are generally unable to provide the diagnostic benefits of the computer program claimed herein due to their inability to produce the scope of colors necessary. In addition, they also lack certain elements of the ideal color manipulation therapy. One such example is the use of lasers and radiation of certain colors on the eye, with the obvious side effects associated with lasers and radiation. Other methods of light therapy involve physically dangerous illumination apparatuses such as gas or flame, which are dangerous and prohibit unattended or at home use due to their very nature. None of these factors are an issue with the current claimed invention.

SUMMARY OF THE INVENTION

It is therefore an object of the current invention to use current and future computer and telecommunication handheld and mobile devices as a method of transportable rehabilitation, light therapy treatments, and a diagnostic device. The use of a handheld device is especially useful in this regard as these handheld devices have a life use beyond the rehabilitation of the patient, and are often distributed to those with neurological impairments by disability agencies making the procurement of such a device far more cost effective than any other rehabilitation device currently available.

Software that is intended for rehabilitation can be adapted for handheld device use. Such software can be purchased or downloaded to the handheld device via the Internet or from the rehabilitation office. This allows the rehabilitation office to provide consistent rehabilitation when a patient is unable to attend. This would require a software suite available to the office, as well as a website for download of software to the handheld device.

It is still a further object of the present invention that it provides a computer display for visually-impaired users that is convenient, lightweight, low-cost, minimally power hungry, and capable of portable operation without degraded performance.

In addition to the objects above, and in all handheld or otherwise portable devices useful in the present invention, less portable means of display such as laptop computers, desktop computers, televisions, or any other telecommunication or display device are also useful in the present invention.

A color light therapy computer method and apparatus has been produced with the capability to display a full range of wavelengths systematically delineated of the visual spectrum. Using said program claimed herein as a foundation application, with various modifications, the preciseness of the wave length production and display thereof allows for a diagnostic process and a host of rehabilitative and treatment applications to be produced from the same fundamental program.

BRIEF DESCRIPTION OF THE DRAWINGS

The above-mentioned features and objects of the present invention will become more apparent with reference to the following description taken in conjunction with the accompanying drawings wherein like reference numerals denote like elements and in which:

FIG. 1 is a table illustrating the visible colors spectrum shifting combinations used in a computer program for a computer capable of at least 256,000,000 colors;

FIG. 2 is a block diagram for an apparatus in accordance with the teachings of the present invention;

FIG. 3 is a flow diagram illustrating the method of present invention; and

FIG. 4 is a flow diagram illustrating the shifting of the combination of the visible color spectrum in a computer program of the present invention.

DETAILED DESCRIPTION OF THE INVENTION

Although the visual system has been traditionally looked at as a sensory system to provide information about detail and spatial awareness, research has also documented that the eyes deliver important photopic information to brain centers which affect hormonal imbalance, diurnal cycle for sleep regulation, and metabolic function. John Ott has described in his research that various wavelengths in the photopic spectrum have significant affects on the growth of plants as well as human biological functions.

The human eye responds to a visual spectrum between 400 nanometers and 700 nanometers. The change in wavelength is processed by the brain through the eyes and establishes the perception and interpretation of color. Shorter wavelength is perceived in the blue end of the spectrum while longer wavelength is perceived in the red end of the spectrum. It has also been documented that the retina of the eye is characteristically sensitive to long wavelengths in the central or macular region of the eye, while the peripheral part of the retina is more sensitive to short wavelengths or the blue spectrum.

Two visual processing centers have been found in the brain. The occipital cortex is the primary area of the brain for establishing imagery and detail detection through central macular involvement. This portion of the visual system and brain relays information to higher cognitive and perceptual processes. This has been called the focal vision process. A second visual process relays approximately 20% of all of the sensory nerves from the eyes to a lower portion of the brain known as the midbrain or thalamus. It is here that the peripheral information received from the eyes is relayed and matched with balance and movement centers such as the kinesthetic, proprioceptive, and vestibular processes. This portion of the visual system has been called the ambient vision process. It organizes information related to spatial function for support of balance and anticipation of movement. This is the first part of the visual process that must respond to visual stimuli. Once information is matched between the ambient and sensory motor processes, it is feed-forwarded to the occipital cortex and 99% of the higher cerebral cortex. The purpose of which is to relay information particularly to the occipital cortex in order to pre-program it how to see the world spatially or more as a whole. It is responsible to establish relationships among the details as well as to spatially coordinate binocular integration cells to blend and merge the separate images of each eye into one. This process is called fusion.

It is also determined that the focal and the ambient process not only respond to different wavelengths of the visual spectrum, but that they also organize a temporal component related to spatial function in two different manners. The focal process will tend to isolate and upon doing so, will attempt to slow time or temporal relationships. The ambient process conversely tends to speed up temporal relationships. A simple experiment will demonstrate this. If a drum with vertical stripes is rotated at a constant speed, one will perceive the speed of the stripes differently if they concentrate hard on each stripe and attempt to focalize the visual process compared to if they relax and attempt to stare through the drum not concentrating on each stripe. The focal process when engaged will cause the person to perceive that the rotating stripes will appear to slow down in temporal context whereas when staring through the drum and not concentrating on the stripes, the ambient visual process will tend to cause the subject to perceive that the stripes will speed up temporally.

Understanding that the ambient and focal visual processes are critical for organization of space related to temporal function and that the organization of space and time must be established in order for higher cognitive perceptual processes to function properly, the function of the ambient and focal process in relationship to each other can alter function and performance of the individual and further, any interference neurologically with the relationship established between these two processes will interfere with aspects of spatial orientation, perceptual motor function, cognitive function, and higher perceptual interpretation.

Following a neurological event such as a cerebrovascular accident (CVA), traumatic brain injury (TBI), multiple sclerosis (MS), cerebral palsy (CP), autism, etc., interference can alter the relationship between the ambient and focal process. This can cause a wide range of dysfunctions as well as symptoms. Characteristics of the dysfunction visually are that imbalances will occur in oculomotor function such as strabismus (ocular deviation) or variation in phoria (tendency for the eyes to deviate in alignment). Problems with convergence, accommodation, and sensory motor function for pursuit tracking and saccadic fixations are often evident. Also, following a neurological event that is related to higher brain dysfunction, a visual field loss will often occur affecting the common field projected by each eye such as with a homonymous hemianopsia. In this condition either the complete right or left visual field will be lost. The field loss, in turn, affects concepts of visual midline. When the visual midline shifts, individuals will then attempt to lean to one side and drift during ambulation.

To perform the functions described above, an apparatus shown in block diagram in FIG. 2 is utilized. This apparatus utilizes a color display or array 2 which is fed with the display output of a central processing unit 4. This central processing unit 4 may be any computer device such as a desktop computer, laptop, etc., which includes at least a microprocessor, random access memory, a keyboard, a semi-permanent storage system and a color display driver. As an input to the CPU 4 is clinician input 6 which may be the keyboard of the CPU 4 or some other device such as a touch screen, mouse, joy stick, etc. The CPU 4 is capable of providing data output directly to a portable device 8 such as a laptop computer, PDA, etc. Another data output of the CPU 4 goes to a conversion means 10. The conversion means 10 may comprise a program within the CPU 4 for converting data stored in the CPU 4 into a format capable of being handled by other devices such as laptop computer, PDA's etc. belonging to or leased by the patient and then storing it on a floppy disk, CDROM, DVD, tape, etc. In addition, the conversion means 10 may also comprise a means for providing an interface between the CPU 4 and a local area network, internet, phone line, etc.

It should also be apparent to one of ordinary skill in the art that a new and "intelligent" devices with more computing capability are created such as intelligent VCR's, CDROM players and DVD players that the function of the device described above and the patients device could incorporate or in fact be such "intelligent" devices.

Referring to FIGS. 1-4, a mode of therapy for persons who have experienced a neurological event or a neurological dysfunction which interferes with the processing of ambient or focal image system, will be described in the numbered paragraphs 1-5 below.

1. The patient will be seated before a visual display 2 such as a television, CRT or LCD monitor, which will provide specific wavelengths that are perceived by the visual process as variation in color. The patient will be seated between 15-25 inches from the monitor. The display 2 will be adjusted using the clinician input 6 to provide initially a balance between the blue or short wavelength end of the visual spectrum and the red or long wavelength of the visual spectrum. For patients who have experienced a neurological event or cause that interferes with the ambient visual process, treatment will then be shifted to the blue end of the spectrum by the clinician. The patient will be given three five-minute therapy sessions exposed to short nanometer wavelengths of light.

2. The apparatus will then be adjusted through the clinician input 6 to the CPU 4 to shift from the blue end of the spectrum toward longer wavelengths. The design of the apparatus will enable the clinician to develop gradation shifting across the spectrum in a variety of ways as shown in FIG. 1 such that blue can be shifted in wavelength toward various spectrum portions such as green, yellow, or red in accordance with the flow diagram of FIG. 4. This will enable the clinician to be very specific in delivering the direction of the therapy toward specific aspects of motor function, cognitive function, or higher perceptual processes. For example, shifting from blue to red will be oriented to bring spatial relationships to development of figure/ground relationships and perceptual constancy. Shifting to the yellow end of the spectrum will have more specific function related to movement, object localization, and perceptual transformations. Shifting from blue toward the green end of the spectrum will be more related to affecting those patients who are experiencing a highly focalized nature to their vision such as in autism where the visual system will fragment the world into detail or parts. While FIG. 1 is described in terms of at least 256,000,000 possible colors, it should be apparent to one of ordinary skill in the art that the present invention would function with less color combinations.

3. A temporal component will be added to the color relationship by establishing a stroboscopic affect to the color presentation via clinician input 6. For those patients who are highly focalized, blue light will begin in a very high stroboscopic affect since the ambient visual process has a higher critical fusion frequency that the focal process. The stroboscopic affect will be slowed as the wavelengths of light are shifted in the direction of the target and the spectrum from the short wavelengths. For those patients who are highly distractible, the temporal component will be started very slowly and increased toward the higher critical fusion frequency. This step could also include the use of multiple strobes or can be even be used without a strobe if either of these options is considered beneficial.

4. For those patients who are experiencing neurological dysfunction as related to attention deficit disorders, the color or wavelength variation will be shifted from red, yellow, or green toward the blue end of the spectrum in a similar manner described in method one (1). The temporal component will also be altered related to the critical fusion frequency of the focal or ambient process.

5. For those patients who have experienced a neurological event causing a visual field loss such as a homonymous hemianopsia, the clinician will adapt the display 2 so that half the portion of the screen will provide a color function while the other half of the screen will provide color and a stroboscopic affect. The stroboscopic affect will be delivered to the portion of the visual process that is in the homonymous hemianopic field. For patients with a field loss on the left side, a slow to rapid stroboscopic affect will be provided while fixation will be centered on a target in the middle of the screen. This is to establish half of the visual field in continuous wavefront modulation while the other half of the field related to the scotoma or field loss would be provided wavefront modulation in a stroboscopic affect. The stimulation in the stroboscopic affect as well as specific nanometers will be used therapeutically in an attempt to reestablish a temporal and spatial relationship of those cortical brain cells that no longer are matching information between focal and ambient processing.

Frequently, patients who have suffered a CVA or TBI will have a homonymous hemianopsia. Stimulation of that field repeatedly will cause the cortical cells to reestablish the visual process in the affected field. The wavefront modulation system is designed as a therapeutic mechanism to treat these visual problems that up to this time no methodology or instrument invention has been found to improve function.

Referring further to FIG. 3, in operation the clinician will start the apparatus and provide initial operator input into the apparatus. Based on this initial input by the clinician, the color display 2 will be adjusted to provide the correct colors, shift and stroboscopic affect. After the patient has been exposed to the color display 2 for the required time, typically 5 minute sessions, the effect of the color therapy will be observed by the clinician who will determine whether or not the therapy is now at an optimum level. If no, there will be further adjustments made and if yes, the optimum color therapy program which has been developed during the session or sessions will be stored in the CPU 4. So that the patient can utilize this optimum color therapy program developed during the session or sessions, the optimum color therapy program for this particular patient which is stored in the CPU 4 will be then either directly transferred to the portable device 8 of the patient or sent to the conversion means 10 for conversion either to a program in the format usable by the portable device of the patient or into a format which can be transferred over the internet, a local area network, telephone line, etc., to be accessed by a patient at a remote location. The control program for the operation shown in FIG. 3 can be easily created by one of ordinary skill in the art based upon the flow diagram of FIG. 3.

By providing the patient with the means for utilizing the optimum color therapy program developed specifically for the patient on a device in the possession of the patient and at a location and times of the patient's choice, many of the disadvantages of the prior art can be overcome.

Still further, the apparatus and method of the present invention provides one or more of the following:

1) A method of diagnosis of optimal color wavelengths for devising an exact therapeutic prescription including nanometer specifications and hue-saturation to prescribe for individuals with a wide range of visual problems, including but not limited to learning disabilities and neurological problems.

2) A computer-implemented method for assisting a user in cognitive and vision rehabilitation, as well as the rehabilitation and assistance of learning disabilities via a handheld device to assist the visually impaired, learning impaired, as well as those in need of cognitive rehabilitation due to brain injury, stroke, CVA or other neurological injury or disease.

3) Adaptations of current rehabilitation software as outlined in other patents by the same inventors (Dara Medes, Heather Medes, William Padula) to be downloaded onto a handheld device.

4) A website to make said software suite available for download onto a handheld device.

5) A CD, DVD and any such other recordable medium devices to hold such software for distribution.

6) The software processes of converting rehabilitation software from dumb-terminal non-portable systems to software that is portable via any handheld or telecommunication device.

7) Neurological Treatment methods in or outside of traditional rehabilitation setting by using said software suite to do rehabilitation in a setting and schedule most convenient to the patient.

8) Treatments traditionally associated with light therapy including but not limited to vision therapy, sleep disturbance, headaches, asthma, depression, weight problems, adrenal and hormonal imbalances, dermatological enhancement, cosmetic enhancement, amongst others, can be available in a portable form not requiring constant office supervision.

9) Treatment services traditionally restricted to directly out of a doctor's office may now be monitored via wire or wireless telecommunication or processing devices, including any other form of transmission technology, or in a doctor's or therapist's office setting. This allows for treating the house bound or those geographically far away in or out of a traditional office treatment setting.

The above description is for the purpose of teaching the person of ordinary skill how to practice the present invention, and it is not intended to detail all obvious modifications and variations of it, which will become apparent to the skilled worker upon reading the description. It is intended, however, that all such obvious modifications and variations be included within the scope of the present invention, which is defined by the following claims.

The invention claimed is:

1. A color shift therapy apparatus comprising:
a control means;
a color display means for being viewed by a patient; and
a driving means for at least providing color shifting signals to said color display in response to said control means for displaying gradation shifting colors on said color display means;
whereby in response to said control means a color shift from one preselected color to another preselected color is repeatedly performed while changing said one preselected color and said another preselected color until an optimum color therapy program of the correct colors and gradation shift is determined; whereby said gradation shift between the correct colors is to be repeatedly displayed in therapy.

2. The color shift therapy apparatus according to claim 1 wherein said control means comprises a clinician input means.

3. The color shift therapy apparatus according to claim 2 wherein said clinician input means comprises at least one selected from the group consisting of a keyboard, a mouse, a joystick and a touch screen.

4. The color shift therapy apparatus according to claim 1 wherein said means for providing color shifting signals comprise a central processing unit.

5. The color shift therapy apparatus according to claim 4 wherein said color display means is selected from the group comprising of CRT, LCD and a television.

6. The color shift therapy apparatus according to claim 5 wherein said display means is capable of displaying 256 million possible colors.

7. The method for providing color shift therapy with the apparatus of claim 1, said method comprising the steps of:
placing a patient in front of the color display;
providing initial clinician input to the control means to display colors and gradation color shifts on the color display;
having said patient view said colors and gradation color shifts on said color display;
determining if said colors and gradation color shifts have a desired effect on said patient; and
changing said colors and gradation color shifts until said desired effect occurs;
whereby said gradation color shifts between said colors, having said desired effect, is to be repeatedly displayed in therapy.

8. The method according to claim 7 further comprising creating and storing an optimum therapy program for said patient when it is determined that said colors and color shifts are having the desired effect on patient.

9. The method according to claim 8 further comprising providing one optimum therapy program to said patient for use on said patient's own remotely usable apparatus.

10. The method according to claim 7 further comprising the steps of transmitting said optimum color therapy program to a remote device.

11. The method according to claim 7 further comprising the step of providing a stroboscopic effect on said color display.

12. The color shift therapy apparatus according to claim 1 wherein said control means further controls said driving means to provide stroboscopic signals to said display means to cause said gradation color shifting to occur with a stroboscopic effect.

13. The color shift therapy apparatus according to claim 1 further comprising a means for transmitting said optimum color therapy program to a remote device.

14. The color shift therapy apparatus according to claim 13 wherein said optimum color therapy program is transmitted to a remote device via Internet.

15. The color shift therapy apparatus according to claim 1 further comprising a means for storing said optimum color therapy program and for transferring said optimum color therapy program to a detachable apparatus for using said optimum color therapy program at remote locations by said patient.

* * * * *